United States Patent [19]

Schlöndorff et al.

[11] Patent Number: 5,186,174
[45] Date of Patent: Feb. 16, 1993

[54] PROCESS AND DEVICE FOR THE REPRODUCIBLE OPTICAL REPRESENTATION OF A SURGICAL OPERATION

[75] Inventors: Georg Schlöndorff, Roetgen; Ralph Mösges, Munich; Dietrich Meyer-Ebrecht; Philipp Moll, both of Aachen, all of Fed. Rep. of Germany

[73] Assignee: G. M. Piaff, Kaiserslautern, Fed. Rep. of Germany

[21] Appl. No.: 445,838

[22] Filed: Jan. 29, 1990

[30] Foreign Application Priority Data

May 21, 1987 [DE] Fed. Rep. of Germany ....... 3717871

[51] Int. Cl.⁵ .............................................. A61B 19/00
[52] U.S. Cl. ................................. 128/653.1; 606/130; 378/4
[58] Field of Search ................. 128/653 R, 653.1; 606/130; 378/4, 20, 205

[56] References Cited

U.S. PATENT DOCUMENTS

| | | |
|---|---|---|
| 4,465,069 | 8/1984 | Barbier . |
| 4,583,538 | 4/1986 | Onik et al. ..................... 128/653 R |
| 4,791,934 | 12/1988 | Brunnett ......................... 128/653 R |
| 5,016,639 | 5/1991 | Allen .................................. 606/130 |
| 5,050,608 | 9/1991 | Watanabe et al. .............. 128/653 R |

FOREIGN PATENT DOCUMENTS

| | | |
|---|---|---|
| 0018166A1 | 4/1980 | European Pat. Off. . |
| 0207452 | 6/1986 | European Pat. Off. . |
| 3205915A1 | 2/1982 | Fed. Rep. of Germany . |
| 3205085A1 | 2/1991 | Fed. Rep. of Germany . |
| 2094590 | 9/1982 | United Kingdom ................ 606/130 |

OTHER PUBLICATIONS

Journal Igaku-no-Ayumi, Medical Progress, vol. 137, No. 6, May 10, 1986, Hideyasu Watanabe: Neuronavigator.

Primary Examiner—Kyle L. Howell
Assistant Examiner—Krista M. Pfaffle
Attorney, Agent, or Firm—McGlew and Tuttle

[57] ABSTRACT

The process comprises the steps of creating three reference points at an object and taking a tomogram of the object such that the three reference points define a first set of positional data in the tomogram. The object is then non-rigidly placed on a support for operation thereupon by an instrument which is mounted at a flexible arm containing sensors for sensing the movements of an instrument tip. The instrument tip is placed at the three reference points in order to create a second set of positional data which are in a fixed relationship to the first set of positional data. When the instrument is inserted into the object placed on the support, the positional data of the instrument tip during the insertion movement are sensed and related to the first set of positional data via the fixed relationship between the first and second sets of positional data. The positions of the inserted instrument within the object are thus reproduced in the tomogram for indicating and displaying, monitoring and recording purposes.

10 Claims, 4 Drawing Sheets

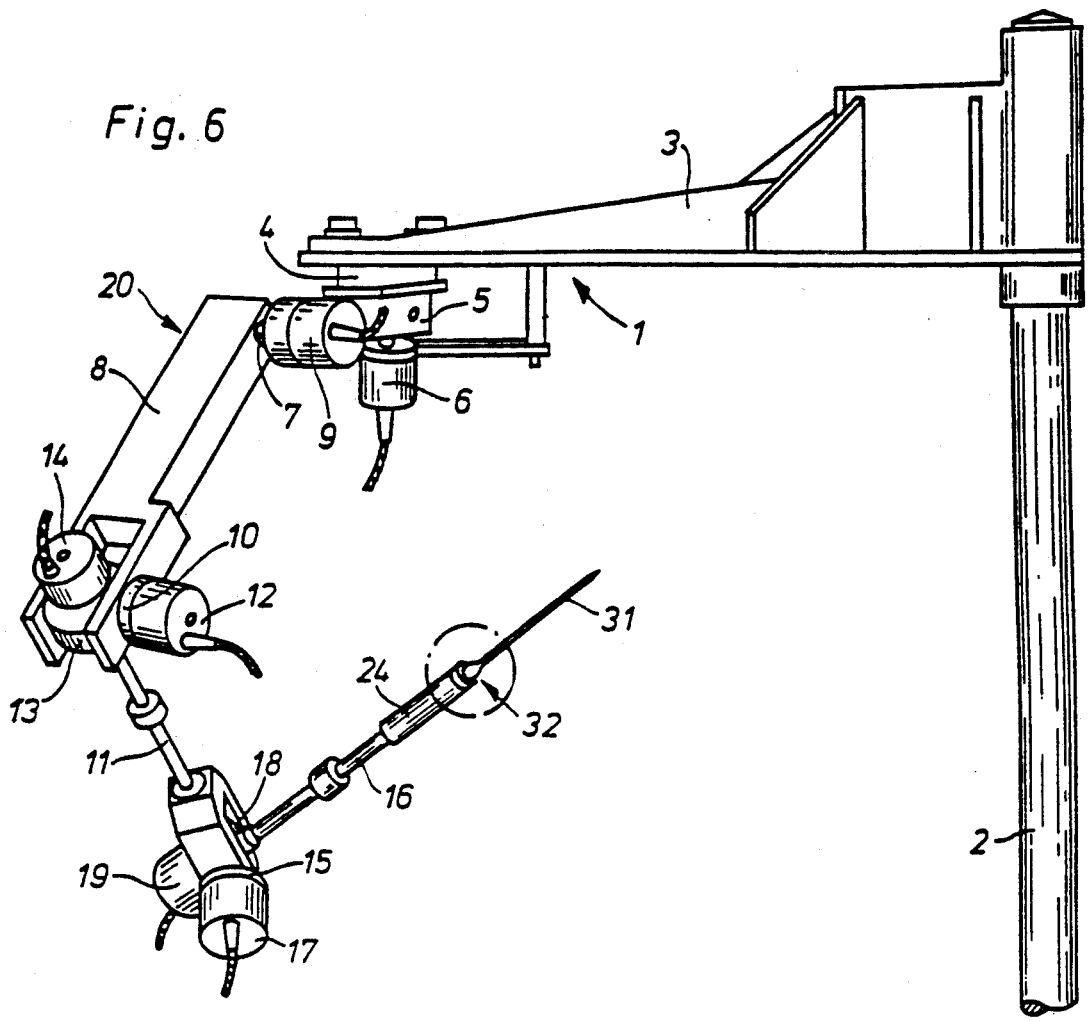
Fig. 6
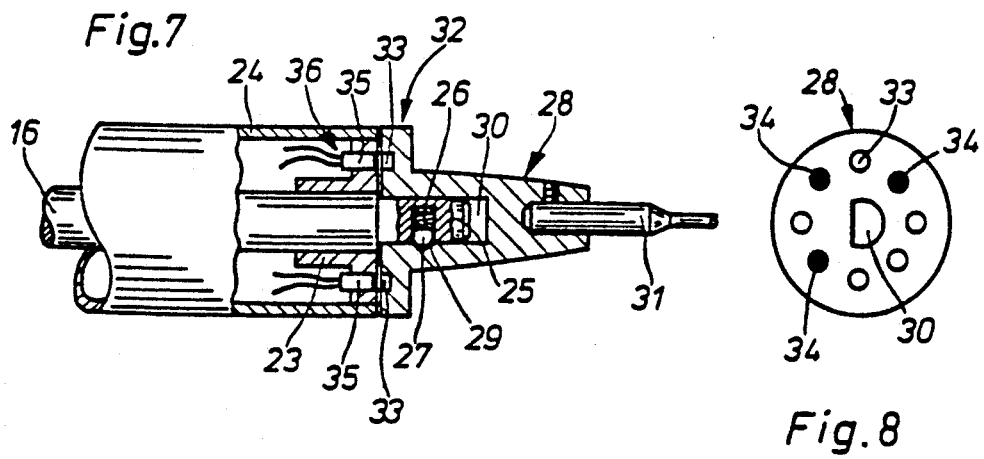
Fig. 7
Fig. 8

PROCESS AND DEVICE FOR THE REPRODUCIBLE OPTICAL REPRESENTATION OF A SURGICAL OPERATION

FIELD OF THE INVENTION

This application is a converted application originally filed on May 21, 1988, as international application PCTG/EP 88/00457, which was originally filed as German national application P 37 17 871.7 on May 27, 1987.

The present invention pertains to a process and a device for representing on a tomogram an indication of the position of an instrument located in an area represented by the tomogram, and in particular to continuously combining measurements of the position of a surgical instrument with previous tomogram images to continuously show the position of the surgical instrument on the tomogram.

BACKGROUND OF THE INVENTION

In many operations, especially in the region of the head, problems may arise in terms of orientation during the operation because of the individual anatomic variations. There are numerous operations in which increased risk can be observed solely because of the problem of comprehensive, accurate orientation during the operation.

Continuous information on the position of surgical instruments in a given body part, especially knowledge of the spatial distance from delicate structures, such as blood vessels, lymph vessels, nerves, etc., increases the safety during operation. If it were possible to record and store this information, i.e., to make it reproducible, it would be possible to check the result of the operation after it has been completed. In the case of a failure arising through no fault of the surgeon, it would thus be possible to effectively head off unjustified malpractice suits.

Conventional X-ray pictures, computer tomograms, and/or, in exceptional cases, also intraoperative fluoroscopy have been used and applied so far to make orientation in the human body possible Bony structures are primarily visualized in the X-rays. Using the more condensed information provided by computer tomograms for planning surgery has therefore been common practice. The application of the X-ray findings to the surgical procedure is accomplished by the surgeon. He checks visually the exact position of the surgical instrument intraoperatively. The surgical field is also occasionally measured or transilluminated. The latter is associated with all the disadvantages of the conventional X-ray technique and higher radiation load for the patient and the surgeon. In the case of intraoperative lateral fluoroscopy, another major disadvantage is the fact that the spatial relations in the body area to be operated on can only be represented by the image in the superimposed form. An extremely great wealth of experience is required in order to infer even approximately the actual spatial relations.

However, this does not provide continuous, reliable information on the position of the surgical instrument in relation to the position of the disease. As an alternative to the conventional methods, it is now possible to use computer-aided position information.

In neurosurgery, stereotactic operations are performed using a localization frame and an instrument holder. Such devices have been known, e.g., from West German Offenlegungsschrift (preliminary published patent application) No. 32,05,085, U.S. Pat. No. Specification No. 4,465,069, EP-A-0,207,452, EP-A-0,018,166, and West German Offenlegungsschrift No. DE-OS 32,05,915. A specific V-shaped frame has also become known from U.S. Pat. Specification No. 4,583,538, but it has been designed for and adapted to corresponding operations in the thorax rather than for neurosurgery.

Stereotactic surgery is part of neurosurgery and pertains to a class of operations in which probes, e.g., cannulae, needles, clamps, or electrodes, are to be applied to areas of the brain or other hidden anatomic targets, which are not visible from the outside. The stereotactic frame is used as a kind of "guiding device", which is used in human neurosurgery in order to guide an instrument to a special point within the brain through a small opening in the cranium by radiographic or other methods of visualization of reference points. The instrument must be brought to an exact, predetermined point as accurately as possible. Consequently, if the frame or the device is placed on the cranium, the probe can be moved forward to any given topographic point within the skull. The exact point is subsequently calculated from the distance determined and the direction between the reference point observed and the desired target in relation to the system of coordinates of the stereotactic device. By linearly moving forward the instrument, which is positioned accurately over the instrument holder held in said frame, a specimen is subsequently taken from the desired point, a local lesion is produced, or radioactive material is implanted.

Such methods were further developed in order to automate them as much as possible or in order to use, e.g., a laser coagulator. Punctiform lesions can be produced according to a plan prepared on the basis of computed tomograms. These known processes and devices also require the use of a frame rigidly adjusted to the head. It must also be borne in mind that accurate location of the frame can be achieved only by screwing at least three screws firmly into the cranial bone.

Contactless, i.e., frameless measurement for obtaining computer-aided position information for an instrument has also been known from a paper published in the journal, Neurosurgery, Volume 65, Oct. 1986, pp. 445 ff. According to this process, the exact position of a surgical microscope is determined via three acoustic signal transmitters using air gaps and a total of four receivers. In addition, the computed tomograms previously entered into the memory can be projected into the focal plane of the surgical microscope in order to provide adequate assistance during the operation.

However, as was also mentioned in the previous publication, this process is essentially a stereotactic surgical system which operates only point by point and in which the working point is approached linearly, and, in addition, it can be used essentially only in the region of the cerebral cranium, but not in the bony cranium. This may also be due to the fact that the accuracy specified, exceeding 2 mm, is insufficient.

Furthermore, none of the known processes offer the possibility of documenting, in images, the course and the result of the surgical operation for subsequent checking, or no provisions are made for such documentation in the known processes.

SUMMARY AND OBJECTS OF THE INVENTION

It is an object of the present invention to provide a process and a device which permit, for the first time ever, reproducible representation on a display screen of the tomograms prepared previously, together with the continuous representation of the position of a instrument being moved freely by hand in a three-dimensional model of the body part or object.

This task is accomplished according to the present invention by first creating at least three reference points on the object that can be located by the tomogram and a coordinate measuring device attached to the surgical instrument. A series of tomograms are then taken which show the planar images or "slices" of the object along with the reference points. Next, the coordinate measuring device is used to measure the position of the reference points. The coordinate measuring device measures the position of the reference points with respect to each other and measures the position of the surgical instrument in relation to the reference points. Then the tomograms, along with the information from the coordinate measuring device are fed into a data processing system. The information from the coordinate measuring device describes the location of the surgical instrument in relation to the reference points, and the tomogram shows the relation between the reference points in the different areas of the object. The data processing system combines all this information and displays tomograms superimposing the position of the instrument.

Substantial advantages over the state of the art are achieved through the present invention. First, it is possible to continuously represent, on a display system, the surgical field and its surroundings in the form of sections freely selectable by the surgeon, and the position of the surgical instrument is also superimposed continuously into the representation of the surgical field at the same time, as a result of which so-called superimposition images are obtained.

Since the position is calculated continuously from the coordinates of the instrument holder or the associated coordinate measuring device, this makes repeated X-raying unnecessary even during the operation. This also reduces the X-ray radiation doses compared with the state of the art (intraoperative lateral fluoroscopy). However, it is also possible to use other tomographic methods, e.g., nuclear spin tomography. The process according to the present invention and the device according to the present invention can be used particularly advantageously (but not exclusively) in the region of the facial cranium.

The reproducible image representations can also be documented by taking photographs of the superimposition images visible on the output device continuously. Another advantageous possibility for documentation is to enter the image data of the superimposition images into a data storage unit of the data processing system, from which these data can be polled at any time and again displayed on the output device.

The surgical instrument can be imaged by displaying the position of the tip of the instrument as a point or graticule on the display screen. This mode of representation is fully sufficient for performing the surgical operation, because the surgeon moves the surgical instrument by hand and determines its spatial longitudinal extension. However, it may be useful for documentation of the operation and for the possibility of subsequently checking the course of the surgery to image not only the tip but also at least part of the entire instrument in order for the longitudinal extension and the instantaneous orientation of the surgical instrument to be recognizable on the superimposition image.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 6 is a schematic representation of the coordinate measuring device;

FIG. 7 is a sectional view of a detachable coupling equipped with a code reader for receiving an instrument holder provided with an identification code;

FIG. 8 is a side view of the instrument holder with identification code;

DETAILED DESCRIPTION OF THE PREFERRED EMBODIMENTS

Figure 5:
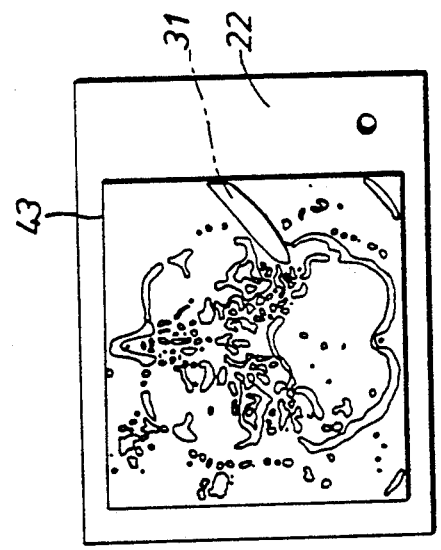
FIG. 5 is a superimposed representation of the surgical instrument processed according to the present invention, with a tomogram.
Figure 3:
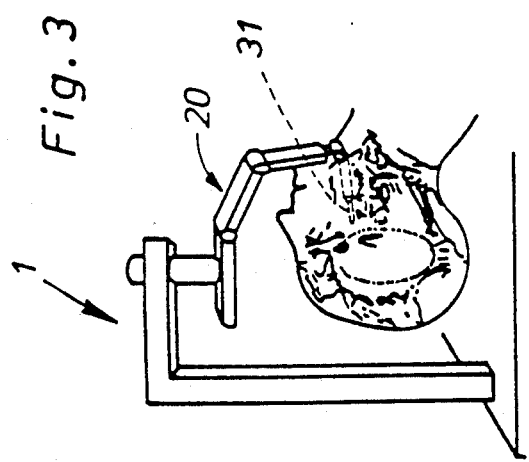
FIG. 3 is a simplified schematic representation of a coordinate measuring device with a surgical instrument in place in conjunction with a patient's body part to be treated.

FIG. 3 shows a simplified representation of a coordinate measuring device 1, whose design is apparent from FIG. 6. The coordinate measuring device 1 has a an extension arm 3 adjustable on a rod 2. Via a joint 4, the extension arm 3 is connected to an arm 5 that can be pivoted in the horizontal plane. A synchro 6, which sends a signal corresponding to the actual angular position of the arm 5, is arranged on the joint 4.

Via a joint 7, an arm 8 that can be pivoted in a vertical plane, is mounted on the arm 5, and the angular position of the arm 8 is detected by a synchro 9. At the other end of the arm 8, which is designed as a fork, a carrier rod 11 is pivoted via a joint 10, and the pivoted position of the carrier rod is detected by a synchro 12. The carrier rod 11 is also rotatable around its longitudinal axis via a joint 13. The rotated position of the carrier rod 11 is detected by a synchro 14.

At the other end of the carrier rod 11, which is designed as a fork, a second carrier rod 16 is mounted rotatably with a joint 15, and the pivoted position of the carrier rod 16 is detected by a synchro 17. The carrier rod 16 is also rotatable around its longitudinal axis via a joint 18. The rotated position of the carrier rod 16 is detected by a synchro 19.

The components 3 through 19 form an articulated arm 20 with six axes of rotation.

Figure 4:
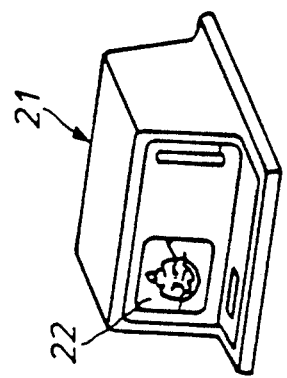
FIG. 4 is a computer with a graphic display screen.

The joints 4, 7, 10, 13, 15, and 18 are designed such that they are self-locking, but can be moved with little force. The synchros 6, 9, 12, 17, and 19 are incremental synchros with 4,000 pulses per revolution. Based on this high pulse count, the angles of the pivoted and/or rotated positions of the corresponding members of articulated arm 20 are detected with very great accuracy. The synchros 6, 9, 12, 14, 17, and 19 are connected via cables without references numerals to a data processing system 21 shown schematically in FIG. 4, which comprises a computer, a data storage unit, and a display screen 22 as an output device.

A flange 23, whose circumferential side is covered by a sleeve 24, is attached to the carrier rod 16 in the zone of its free end. A pin 25, which is flattened on one side, is provided on the carrier rod 16 in the area joining the flange 23. A spring-loaded ball 27, which is secured against falling out by an appropriate narrowing not shown on the edge of a transversely extending blind hole 26 of the pin 25, is arranged in the blind hole 26.

An instrument holder 28, which has a recess 29 associated with the ball 27 and forms a locking mechanism with the ball, is mounted on the pin 25. The holder 28 contains a bore 30, designed to match the shape of the flattened pin 25, as a result of which the holder 28 is secured against rotation. A surgical instrument 31 is fastened detachably in the holder 28. Thus, the holder 28 and the pin 25 form a detachable coupling 32 for connecting the surgical instrument 31 to the articulated arm 20 of the coordinate measuring device 1, which consequently also forms a guiding and holding device for the instrument 31.

The end face of a flange part of the instrument holder 28 is provided with a plurality of blind holes 33 arranged in a circular pattern, in which three permanent magnets 34 are fastened. The array of the permanent magnets 34 forms an identification code associated with the instrument used 31.

Hall generators 35, whose number matches that of the blind holes 33, are located exactly opposite the holes 33 and form a code reader 36, in the flange 23. The permanent magnets 34 cause the Hall generators 35 associated with them to generate a signal. The signals generated by the Hall generators 35 and the code reader 36 are sent to the data processing system 21, as a result of which the system will be informed of the nature and the size of the surgical instrument 31 connected to the articulated arm 20.

Figure 9:
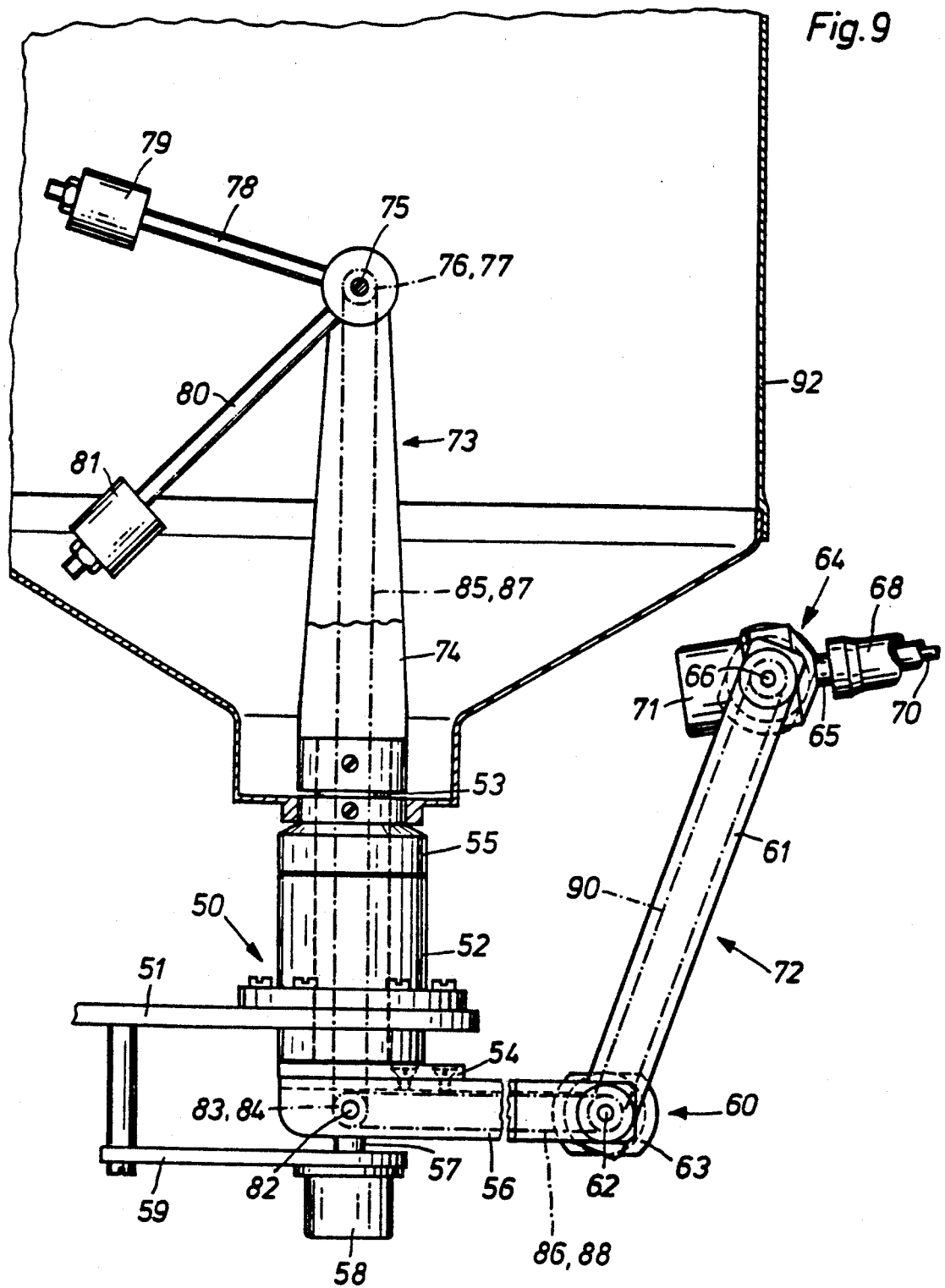
FIG. 9 is a view of part of an articulated arm of a second embodiment of a coordinate measuring device with a weight balancing mechanism.

The coordinate measuring device 50 represented partially in FIG. 9 has an extension arm 51, which is arranged adjustably on a rod not shown. A flange-like joint part 52, in which a hollow hinge pin 53 is mounted rotatably, is attached to the extension arm 51. A support plate 54 standing out transversely is provided at the lower end of the hinge pin 53. An adjusting ring 55, which is clamped on a section of the hinge pin 53 projecting over the joint part 52 and together with the support plate 54, locks the hinge pin 53 axially.

A hollow arm 56, standing out transversely, is fastened to the support plate 54. A pin 57 attached to the arm 56 extends coaxially to the hinge pin 53, and transmits the rotated position of the arm 56 to a synchro 58 which is fastened and secured against rotation on the extension arm 51 via a bracket 59.

Figure 10:
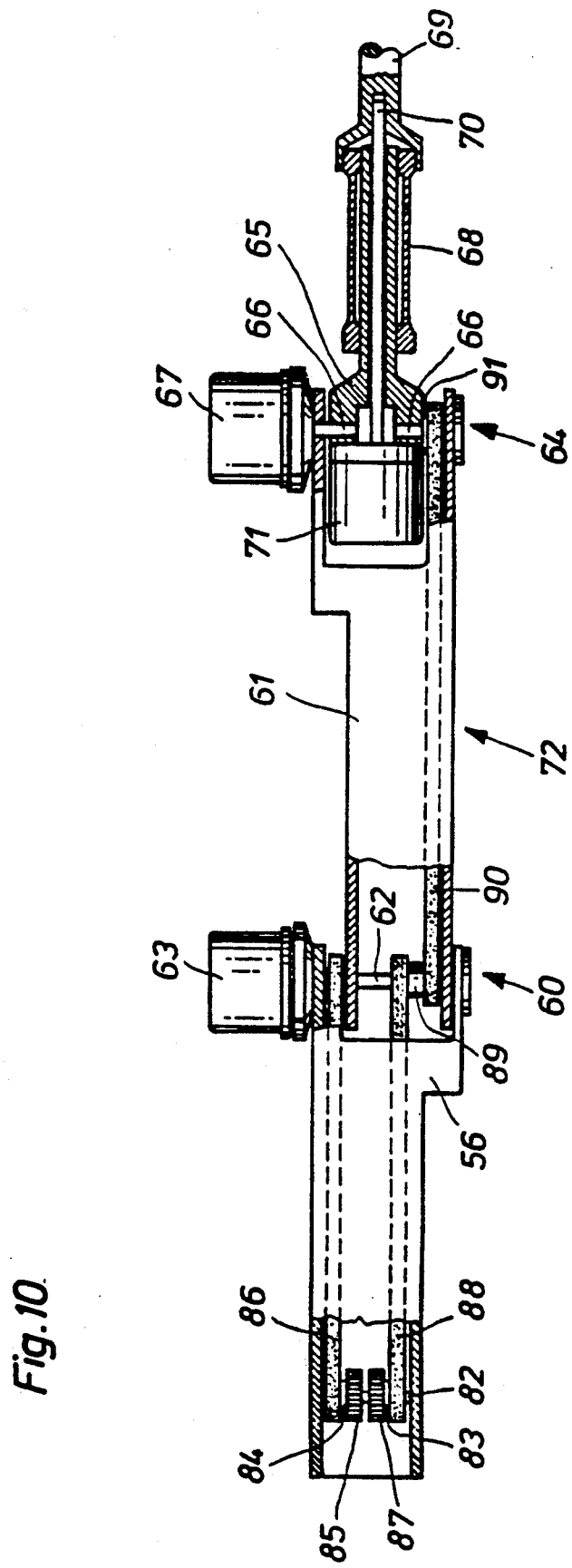
FIG. 10 is a partially cutaway top view of the articulated arm according to FIG. 9, represented in the extended position.

A hollow arm 61, which can be pivoted in a vertical plane and whose angular position is transmitted to a synchro 63 connected to the arm 56 via a hinge pin 62, is mounted on the arm 56 via a joint 60. At the other end of arm 61, a hollow carrier rod 65 is mounted pivotably via a joint 64, and its pivoted position is transmitted to a synchro 67 arranged on arm 61 via one of two hinge pins 66 which are flush with each other FIG. 10. A sleeve 68, which is connected nonrotatably to a second carrier rod 69 FIG. 10, is mounted rotatably on the carrier rod 65. The rotated position of the second carrier rod 69 relative to the first carrier rod 65 is transmitted via a shaft 70 to a synchro 71 arranged on the carrier rod 65.

The components 51 through 71 are parts of an articulated arm 72, which has a design similar to that of articulated arm 20 FIG. 6, and consequently it also has, in addition to these components, another carrier rod not shown that can be rotated in the longitudinal and transverse directions. Like articulated arm 20, the articulated arm 72 has six axes of rotation. An instrument holder not shown, which has the same design as instrument holder 28, is attached to the carrier rod not shown via a coupling not shown corresponding to the detachable coupling 32.

The articulated arm 72 is provided with a weight balancing mechanism 73. The mechanism has a fork-shaped holder 74, which is clamped on the top end of the hinge pin 53 and has a stationary bolt 75 at its top end. Two toothed belt gears 76 and 77 that are freely rotatable independently from one another are mounted on the bolt 75. A rod 78, at the end of which a balancing weight 79 is arranged, is rigidly attached to the front toothed belt gear 76. A longer rod 80, at the end of which a balancing weight 81 is arranged, is rigidly connected to the rear toothed belt gear 77.

A bolt 82, which extends in parallel to the bolt 75, is rigidly arranged in the arm 56, and two double toothed belt gears 83, 84, which are freely rotatable independently from one another, are mounted in the arm 56. The rear toothed belt gear 77 and the inner gear of the rear double toothed belt gear 84 are connected by a toothed belt 85. The outer gear of the rear double toothed belt gear 84 is connected via a toothed belt 86 to a toothed belt gear not shown, which is arranged on the hinge pin 62 and is connected nonrotatably to the arm 61. Based on this design, pivoting movements of the arm 61 are transmitted via the two toothed belts 86 and 85 to the rear toothed belt gear 77, as a result of which the rod 80 with the balancing weight 81 is pivoted in the same direction of rotation. When the arm 61 extends horizontally, rod 80 also assumes an essentially horizontal position, and when the arm 61 extends vertically, it will assume an essentially vertical position. The orientation positions of the arm 61 and the rod 80 are mutually opposite, i.e., the rod 80 is in the lowered position when the arm 61 is raised, and vice versa. If the balancing weight 81 is designed such that the weight of the arm 61 and other components of the articulated arm 81 which it carries is taken into account, the weight will generate a torque that opposes the torque generated by the weight of arm 61 and the components of the pivoting arm 72 which it carries. Due to the balancing of weights, the balancing weight causes the arm 61 to be able to be moved with essentially equal, weak force in the two opposite pivoting directions.

The front toothed belt gear 76 and the inner gear of the front double toothed belt gear 83 are connected by a toothed belt 87. The outer gear of the front double toothed belt gear 83 is connected via a toothed belt 88 to a gear of a double toothed belt gear 89, which is mounted freely rotatably on the hinge pin 62. The other gear of the double toothed belt gear 89 is connected via a toothed belt 90 to a toothed belt gear 91, which is arranged on the front hinge pin 66 and is connected nonrotatably to the carrier rod 65.

The pivoting movements of the carrier rod 65 are transmitted by the toothed belts 90, 88, and 87 to the front toothed belt gear 76, as a result of which the rod 78 with the balancing weight 79 is pivoted in the same direction of rotation. The movement relations between the carrier rod 65 and the balancing weight 79 are now comparable to the above- described movement relations between the arm 61 and the balancing weight 81. If the balancing weight 79 is dimensioned adequately, it generates a torque which is opposite the torque generated by the weight of the carrier rods 65, 69, the sleeve 68, and the components of the articulated arm 72 which are carried by the carrier rod 69. Based on this weight balancing, the carrier rods 65, 69 and the sleeve 68 can be moved with essentially equal, weak force during their pivoting movements around the hinge pin 66.

A two-part, closed housing 92, which encloses the movement paths of the balancing weights 79, 81, is clamped on the adjusting ring 55.

In another embodiment of an articulated arm not shown, the six synchros are accommodated together in a housing comparable to housing 92, and the individual synchros are connected to the individual members of the articulated arm via separate toothed belt or gear drives. Due to this solution, not only is the articulated arm lighter and consequently easier to handle, but it is also more slender, as a result of which the risk of collisions is reduced.

The mode of operation of the device, as well as the corresponding process will be explained in greater detail below on the basis of a typical procedure.

Figure 1:
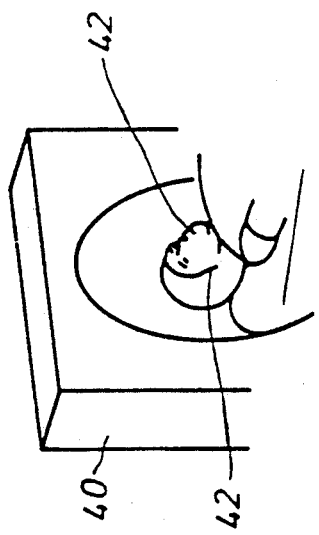
FIG. 1 is a schematic representation for registering a computed tomogram.

A patient to be treated as shown in FIG. 1 is first pushed into a suitable tomograph 40 to register a plurality of tomograms. For example, computed tomograms or, e.g., nuclear spin tomograms may be registered.

Figure 2:
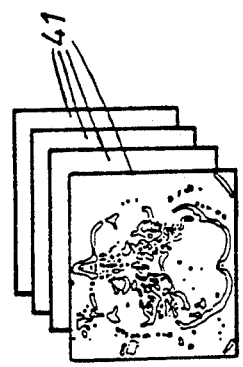
FIG. 2 is tomograms registered on the basis of computed tomography.

FIG. 2 shows schematically the tomograms 41 registered according to FIG. 1.

Prior to the tomography, three reference points 42 are marked, attached, measured, or selected in the area of the body of a patient to be operated on, with two of the three reference points being located in the region of the ears, while the third one may be formed, e.g., by the gap between the two upper incisors, which gap ends in the downward direction.

If it is not possible to select defined reference points because of the actual conditions, it is also possible to insert or apply, e.g., small ceramic parts as reference points in predetermined areas. Small ceramic parts are particularly suitable because they do not cause reflection during the corresponding tomographic procedures.

The above-mentioned reference points 42 are imaged in the corresponding locations and positions in the tomograms 41 shown in FIG. 2, and their data are also recorded. Provided with the data of the reference points, the tomogram data, whose entirety reflects a spatial structure of the object to be treated, are stored in an appropriate memory of the data processing system.

To make preparations for an operation to be performed, the patient is maintained in the supine position on an operating table and adjusted. Before the operation is performed, the positions of the three reference points 42 applied and attached to or selected on the patient's body are determined with the aforementioned coordinate measuring device 1. This is done by bringing the surgical instrument 31 or a tracer used instead of the instrument into contact with the reference points 42, while the instrument or the tracer can be raised, lowered, tilted, angularly adjusted, and moved forward fully unhindered due to the articulation of the articulated arm 20. Any movement and position of the individual members of the articulated arm 20 are exactly detected via the synchros 6, 9, 12, 14, 17, and 19, and sent to the data processing system 21. The position data thus obtained for the reference points 42 are checked against the image data of the measuring points 42 in the data storage unit. As a result of an appropriate computation performed by the computer, the reference points 42, whose positions on the operating table have been determined, are made to coincide with the stored image data of the reference points 42 such that the stored tomogram data are now exactly assigned to the specific spatial position of the patient and especially of the surgical instrument 31.

Using the signals transmitted from the code reader 36, the data processing system 21 polls the code values concerning the size of the surgical instrument and the distance between its tip and the instrument holder 28. These values are associated with the surgical instrument in question and are stored in the data storage unit. After which the exact position of the tip of the instrument is computed by the computer for each of the different instruments in any desired position of the instrument holder 28. After the three reference points 42 have been touched with the coordinate measuring device 1 and the exact spatial relation between the surgical instrument 31 and the patient's body has been established in agreement with the stored tomograms 41, the operation can begin. The tip and the effective zone of the surgical instrument can now be detected via the coordinate measuring device 1 and determined by the computer during a movement and a corresponding surgical procedure, however small the linear and/or angular movement may be. This detected movement of the surgical instrument is subsequently displayed via the computer on the display screen 22, together with the tomogram that is of interest at a given point in time. As a result a superimposition image 43 is obtained.

To document the course of the surgical procedure, the image data of the superimposition images 43 are entered into a data storage unit, from which they can be polled at any time and displayed on the display screen 22.

As soon as the tip of the instrument, due to any further displacement, penetration, or rotation of the surgical instrument moves out of the tomogram presently represented on the display screen, the tomogram currently displayed is automatically replaced with the tomogram into which the tip of the instrument is now penetrating. Thus, the surgeon obtains maximum information on the exact field in which he is working during the operation.

Another measure aimed at providing better information on the spatial position of the tip of the instrument within the operating field can be realized by displaying simultaneously superimposition images, which were obtained from longitudinal, transverse, and horizontal tomograms, in different windows of the display screen 22.

The aid offered by the device described here can be further increased by the possibility of displaying in advance, e.g., one of the next, deeper layers on the display screen 22, if needed, in order to decide first in what direction the surgical instrument 31 should subsequently continue its movement. This also considerably improves safety compared with conventional processes and devices.

Consequently, the coordinate measuring device 1 described is used in this case to detect not only the position of the surgical instrument holder 28 and the instrument 31 itself, but also the three reference points 42. This offers the further advantage that it is possible at any time during the operation to check whether the patient has remained in the correct position. To check this, it is only necessary also to touch the three reference points 42 via an instrument during the operation, and to feed the corresponding position data into the computer. If a slight change in the position of the object being treated is observed, this change in position can be calculated immediately, and the image displayed on the display screen 22 can be corrected.

In the embodiment shown, the surgical instrument of the coordinate measuring device 1 is mounted detachably on or is connected to the articulated arm 20. However, it is also possible to continuously monitor the surgical instrument according to a contactless method via a "locating device", i.e., a coordinate measuring device, and to thus determine the exact coordinates of the position of the tip and of the active area of the instrument and to send these data to the computer. This can be realized, e.g., with three probes arranged in a three-dimensional arrangement and three detectors.

Whether the position coordinates are determined acoustically, optically or electromagnetically e.g., above or below the wavelength range of light depends on the particular case.

If certain body parts are removed with the surgical instrument, the data obtained by tracing the cavities thus formed in the form of an envelope curve can be fed into the data storage unit during the operation and the tomogram data obtained prior to the operation can be modified accordingly. It is thus possible to display on the display screen 22 the actual relations that have changed during the operation. The postoperative tomograms thus obtained are also stored in the data storage unit for documentation of the result of the operation.

While specific embodiments of the invention have been shown and described in detail to illustrate the application of the principles of the invention, it will be understood that the invention may be embodied otherwise without departing from such principles.

We claim:

1. A process for representing on a tomogram positions of an instrument located in an object represented by the tomogram, the process comprising the steps of:
   creating three reference points on the object;
   creating a tomogram of the object, said tomogram encompassing a predetermined number of tomogram slices, at least one of said tomogram slices containing said three reference points;
   storing a first set of positional data associated with said three reference points included in said at least one tomogram slice;
   placing said object in a non-rigid manner on a support;
   positioning an instrument at said three reference points on said object which is placed on said support, and defining a second set of positional data associated with said three reference points on said object placed on said support, said defining being done by said positioning;
   establishing a relationship between said first set of positional data and said second set of positional data;
   inserting said instrument into said object placed on said support;
   sensing positions of said instrument along a path of insertion movement into said object in relation to said second set of positional data, said sensing being performed during said step of inserting said instrument into said object;
   using said relationship established between said first and second sets of positional data for transforming said positions of said instrument along said path of insertion movement into said object in relation to said second set of positional data into corresponding positions in relation to said first set of positional data;
   superimposing an indication of said corresponding position of said instrument on said tomogram slices of said tomogram; and
   displaying said tomogram slices containing said superimposed indication of said corresponding positions of said instrument during said step of inserting said instrument into said object in order to indicate in said tomogram slices said corresponding positions of said instrument located in said object represented by said tomogram.

2. A process in accordance with claim 1, wherein:
   said step of creating the tomogram includes creating said tomogram in substantially horizontal and vertical planes with respect to said object; and said step of displaying said tomogram slices entails simultaneously displaying all of said tomogram slices containing said indication of said corresponding positions of the instrument.

3. A process in accordance with claim 1, further comprising:
   storing said tomogram slices containing said superimposed indication of said corresponding positions of said instrument located in the object for retrieval at a later time.

4. A process in accordance with claim 1, further comprising:
   periodically checking said three reference points on said object placed on said support;
   redefining said second set of positional data associated with said three reference points on said object placed on said support by said periodically checking;
   reestablishing said relationship between said first and redefined second sets of positional data;
   using said relationship reestablished between said first and redefined second sets of positional data for transforming said positions of said instrument along said path of insertion movement into said object in relation to said redefined second set of positional data into corresponding positions in relation to said first set of positional data; and
   said step of displaying said tomogram slices entailing a step of displaying tomogram slices containing said superimposed indications of said corresponding positions of the instrument based on said reestablished relationship between said first and said redefined second sets of positional data.

5. A process in accordance with claim 1, further comprising:

defining and representing a predetermined area of operation in at least one of said tomogram slices;

sensing movements of the instrument inserted into said object and defining an area of operation which is operated upon by said instrument in the object;

recording said movements of the instrument inserted into said object and recording said area of operation; and comparing said recorded area of operation defined by said movements of the instrument with said predetermined area of operation represented in said at least one of said tomogram slices.

6. A process in accordance with claim 5, further comprising:

modifying said predetermined area of operation defined and represented in said at least one tomogram slice as a result of said step of comparing said recorded area of operation defined by said movements of the instrument with said predetermined area of operation defined and represented in said at least one of said tomogram slices.

7. A process in accordance with claim 5, further comprising:

forming a cavity in said object as a result of said sensed movements of said instrument inserted into said object;

representing said cavity as an envelope curve;

superimposing said envelope curve onto said at least one tomogram slice containing said predetermined area of operation; and storing said at least one tomogram slice containing said predetermined area of operation and said envelope curve superimposed on said predetermined area of operation;

storing said envelope curve;

creating another tomogram of the object at a later date;

combining said stored envelope curve with said another tomogram.

8. A process in accordance with claim 7, further comprising:

comparing the initially created tomogram with said another tomogram combined with said stored envelope.

9. A process in accordance with claim 1, wherein:

said step of sensing said positions of the instrument along said path of insertion movement into said object entails continuously sensing said positions of said instrument in said object; and said step of displaying said tomogram slices entails continuously indicating in said tomogram slices said positions of said instrument located in said object.

10. A process for representing on a tomogram a position of an instrument located in an object represented by the tomogram, the process comprising the steps of:

creating three reference points on the object;

creating the tomogram of the object, the tomogram including a predetermined number of tomogram slices, one of said tomogram slices containing said three reference points;

identifying locations of said three reference points on said one tomogram slice;

storing a first set of positional data describing said locations of said three reference points on said one tomogram slice;

placing the object in a supple manner on a support;

positioning the instrument at said three reference points on the object placed on said support;

recording a second set of positional data from the instrument defining locations of said three reference points;

establishing a relationship between said first set of positional data and said second set of positional data;

inserting a tip of the instrument into said object placed on said support;

sensing a position of said tip of the instrument along a path of said inserting, said sensing of said position being in relation to said second set of positional data and being performed during said inserting;

mapping said sensed position of said tip of the instrument along said path into a coordinate frame of the tomogram;

superimposing an indication of said sensed position of said tip of instrument on said tomogram slices of said tomogram; and displaying said tomogram slices containing said superimposed indication of said sensed position of the tip of the instrument during said step of inserting the instrument into the object in order to indicate in said tomogram slices said sensed position of the tip of the instrument located in the object represented by the tomogram.

* * * * *

UNITED STATES PATENT AND TRADEMARK OFFICE
CERTIFICATE OF CORRECTION

PATENT NO. : 5,186,174
DATED : February 16, 1993
INVENTOR(S) : Schlondorff et al It is certified that error appears in the above-identified patent and that said Letters Patent is hereby corrected as shown below:

On the title page, Assignee, should read as follows:

[73] Assignee: G.M. Pfaff
                 Kaiserslautern, Fed. Rep. of Germany

Signed and Sealed this

Twenty-fifth Day of January, 1994

Attest:

BRUCE LEHMAN

Attesting Officer     Commissioner of Patents and Trademarks